March 5, 1974 M. R. MULFORD Plant Pat. 3,507
APHELANDRA PLANT
Filed July 11, 1972
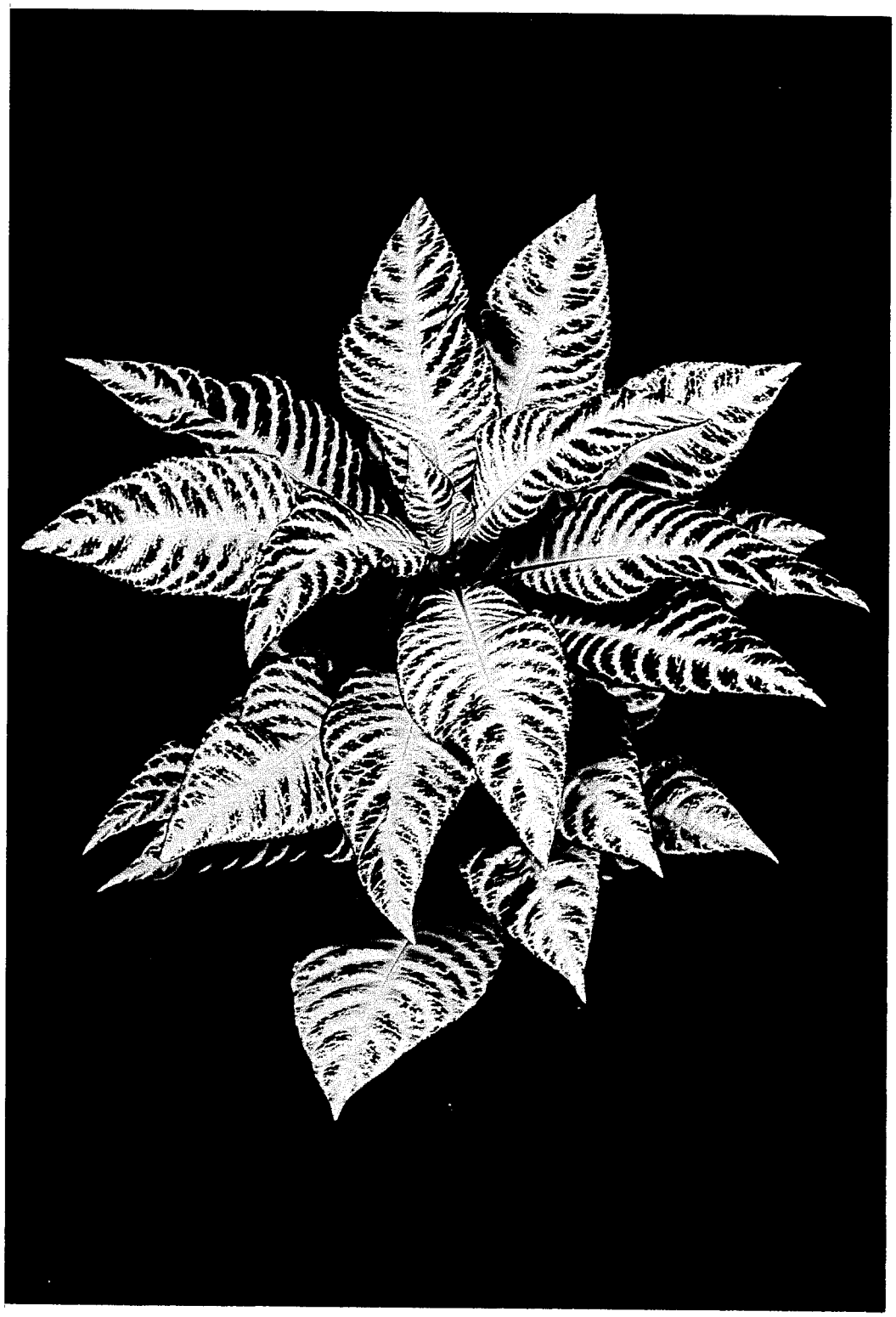

United States Patent Office

Plant Pat. 3,507

Patented Mar. 5, 1974

3,507

APHELANDRA PLANT

Marion R. Mulford, Maitland, Fla., assignor to Norman E. Hickerson, Apopka, Fla.

Filed July 11, 1972, Ser. No. 270,704

Int. Cl. A01h *5/00*

U.S. Cl. Plt.—88 1 Claim

ABSTRACT OF THE DISCLOSURE

A sport of an *Aphelandra squarrosa* plant characterized by distinctive and attractive leaf color which leaves are much whiter in general appearance.

BACKGROUND

The present invention relates to a new and distinct variety of Aphelandra plant which was discovered by me in the greenhouses on the property of Rare Plants, Incorporated, at Altamonte Springs, Fla., as a sport of an Acanthaceae; *Aphelandra squarrosa* "Uniflora Beauty." At the time of my discovery my attention was attracted to a particular plant of the parent variety which was being grown under my direction and control which appeared to be quite different from the parent variety by the color of its leaves which were practically identical with those of the parent except for being much whiter in general appearance, which represents a substantial and valuable improvement over its parent making it more attractive and desirable from a commercial standpoint, which color distinguishes the sport from its parent as well as from other Aphelandra varieties of which I am aware. The white midrib and veins of the leaf of the parent form produce leaves which are dark green above with white midribs and white main lateral veins which leaves are 70 percent or more green and 20 percent to 30 percent white, while leaves of the sport have the same color green but with 25 percent to 30 percent green and 70 percent to 75 percent white.

Asexual reproduction of my new Aphelandra variety was performed by me by cuttings at Altamonte Springs, Fla., and show that the foregoing characteristics and distinctions are fixed and established and come through through succeeding propagations.

DRAWINGS

The accompanying color photographs hown a typical specimen plant of my new Aphelandra variety and in color as nearly true as it is reasonably possible to make the same in a color photograph of this character.

DETAILED DESCRIPTION OF THE PLANT

The following is a detailed description of my new Aphelandra variety as based on observations of specimen plants grown in Altamonte Springs, Fla., and in Apopka, Fla., with color terminology in accordance with The Munsell Color Systems as set forth in Nickerson Color Fan distributed by the American Horticultural Council with the Munsell hue being followed by the value and chroma, except where general color terms of ordinary dictionary significance are obvious.

Parentage: Sport of Acanthceae: *Aphelandra squarrosa* "Uniflora Beauty."

Propagation: Holds its distinguishing leaf colors through succeeding propagations by cuttings.

Plant

This sport is substantially like its parent form in vegetative characteristic which include:

Habit: Herbaceous perennial.

Growth: The full height has not been determined because of the plants being used for cuttings but is expected to range in height from 18 inches to 24 inches with a spread of approximately 14 inches on mature plants; upright and branched.

Stem

Terete with a cross-section from ¼ inch to ½ inch in diameter.

Color: Dark Red, Munsell 5R 3/7.

Nodes: Not noticeably swollen but having a line encircling the same.

Leaves

Parent form: Leaves of the sport are practically identical with those of the parent except for the color, with the parent leaves being mostly opposite, simple, entire or wavy margined; up to 6 inches or more long and up to 3 inches or more wide; ovate to ovate-elliptic with acuminate leaf tips and attenuate leaf base; dark yellowish green above; light yellow-green below, with white midribs and white main lateral veins. This white usually extends out almost to the edge on each side from the midrib making a wide-appearing midrib usually 1/10 inch to ⅕ inch in width. The white main veins with slight extensions of white tissue from the veins themselves usually make white lines as much as ⅕ inch in width.

Sport: In the sport the leaves are practically identical with those of the parent and are simple, opposite blades, ovate to ovate-elliptic, acuminate leaf tips and attenuate leaf bases, and up to 8 inches or more long and up to 4 inches or more wide, with entire or wavy margins and of medium thickness.

Upper surface of blades: Waxy, dark yellowish green, Munsell Hue 2.5 G 3/3 with white extending out from the midrib making the white line varying from 1⅕ inches to 2 inches in width and similar white tissue extending out from the main lateral veins from ⅘ inch to 1½ inches or more on each side. There is a characteristically thin layer of white tissue spreading over still more of the interveinal areas that gradually merges into the interveinal green. Many of the small veinlets between the veins are white. The white tissue is a surface layer of parenchyma overlaying the green beneath it and gradually thinning out as it approaches the midvein point. The result is that the white midrib and veins are 20 to 25 percent green and show 70 to 75 percent white, depending on the age of the leaves and growing conditions of the plant. The color varies with the younger blades being moderate yellow green to moderate olive green, Munsell 5 GY 5/6 to 5 GY 4/3, and some younger blades showing some red as may be seen from the color photograph.

Undersurface: Moderate olive green, Munsell 2.5 GY 4/3 on mature leaves with much less white along the midrib and main lateral veins with a white line varying from ⅛ inch to ¼ inch width along the midrib and the white line along the main lateral veins forming a line from 1/16 to ⅛ inch, with the white varying with the edge of the leaf and growing condition of the plant.

Petiole: ¼ inch to ½ inch terete except for being generally flattened above; stout from ⅛ inch to 3/16 inch in diameter; varying between light yellow green and light yellowish green corresponding to Munsell 7.5 GY 9/4 and 10 GY 8/7 with splatterings of dark red, Munsell 5R 3/7, especially near the base.

Flowers

Parent and similar varieties are flowering plants, but this sport has been observed to flower only rarely with the flowers being identical with the parent and pale yellow with long spikes having yellow bracts.

I claim:

1. A new and distinct variety of Aphelandra plant substantially as herein shown and described, characterized particularly as to novelty by a distinctive and attractive leaf-color having an upper surface layer of parenchyma of white over-laying the green beneath it and extending from the midrib and the main lateral veins to cover a substantial portion of the interveinal area.

No references cited.

ROBERT E. BAGWILL, Primary Examiner